Figure 1:
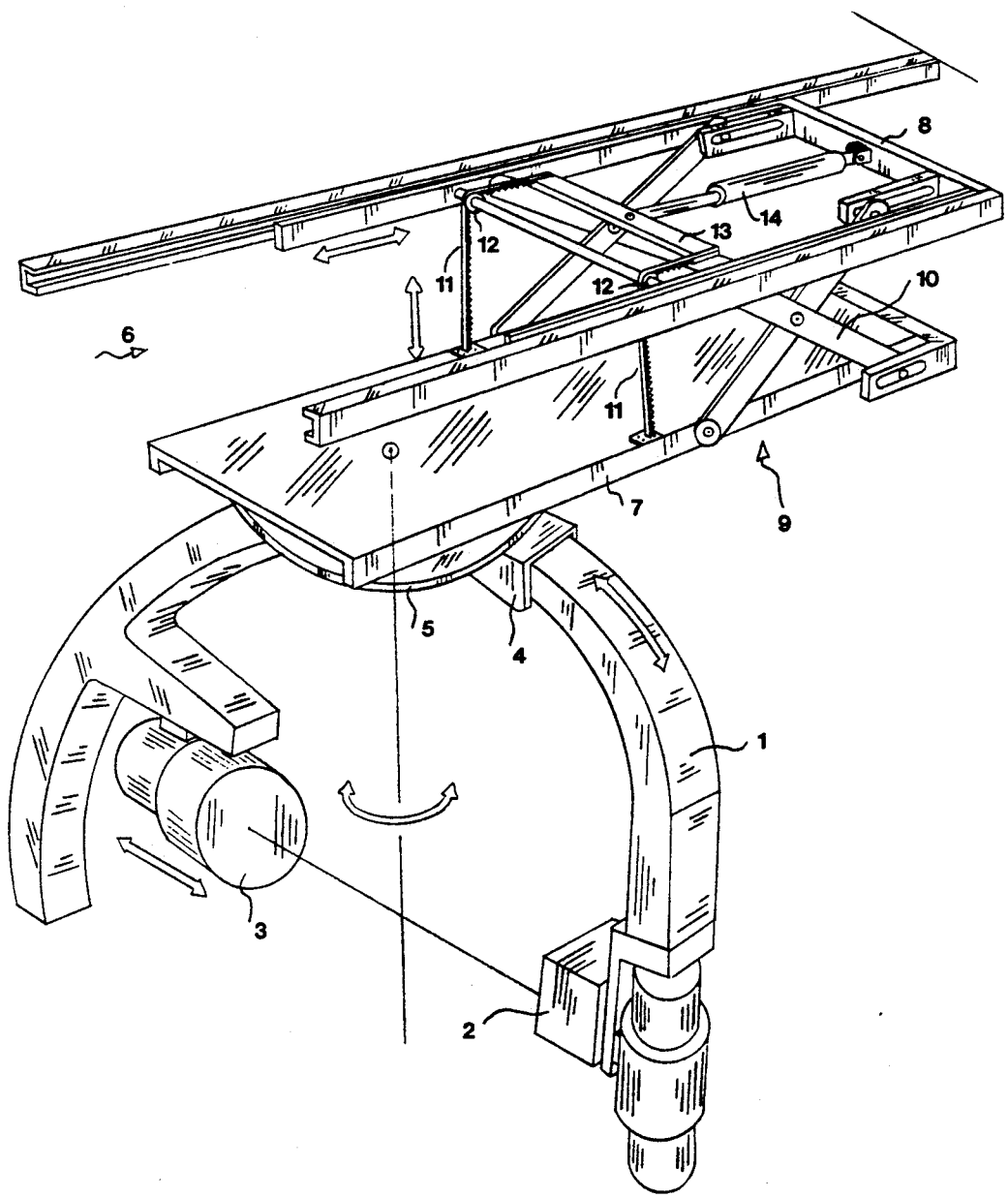

United States Patent [19]

Siczek et al.

[11] Patent Number: 5,086,447
[45] Date of Patent: Feb. 4, 1992

[54] OVERHEAD X-RAY APPARATUS FOR IMAGING IN BI-PLANE CONFIGURATION

[76] Inventors: Aldona A. Siczek; Bernard W. Siczek, both of 1252 Chinook Way, Boulder, Colo. 80303-1411

[21] Appl. No.: 533,155

[22] Filed: Jun. 4, 1990

[51] Int. Cl.$^5$ .............................................. H05G 1/02
[52] U.S. Cl. ..................................... 378/197; 378/193; 378/196; 378/198
[58] Field of Search ................ 378/193, 197, 198, 196

[56] References Cited

U.S. PATENT DOCUMENTS

| | | | |
|---|---|---|---|
| 2,595,260 | 5/1952 | Hollstein | 378/197 |
| 4,802,197 | 1/1989 | Juergens | 378/197 |
| 4,868,845 | 9/1989 | Koropp | 378/197 |

FOREIGN PATENT DOCUMENTS 2621238  4/1989  France ............................ 378/197

Primary Examiner—Carolyn E. Fields
Assistant Examiner—David P. Porta

[57] ABSTRACT

An overhead X-ray apparatus for imaging in the bi-plane configuration which apparatus has the radiation isocenter vertically displaceable. A C-arm (or a like) for supporting an X-ray tube and image receptor is mounted on a carriage assembly in a rotatable arrangement about a vertical axes. The carriage assembly comprises a support frame and a slideable support mounted on overhead rails coupled by a scissor mechanism. A distance between the support frame and the slideable support and, hence the vertical position of the radiation isocenter can be varied by action of chains or timing belts connecting the support frame with the anchoring member which moves along the slideable support while actuated by an actuator.

2 Claims, 1 Drawing Sheet

OVERHEAD X-RAY APPARATUS FOR IMAGING IN BI-PLANE CONFIGURATION

FIELD OF INVENTION

The present invention relates to an overhead mounted X-ray apparatus for imaging in bi-plane configuration, which apparatus includes: an arcuated structure supporting an X-ray tube and an X-ray image receptor for imaging in one of the two planes, a carriage assembly having the arcuated structure mounted thereon, which carriage assembly is slideably mounted on ceiling rails and provides a vertical displacement of the radiation isocenter defined by the X-ray tube and the X-ray image receptor.

BACKGROUND OF THE INVENTION

There has been a growing need for X-ray imaging in bi-plane configuration, particularly for cardiac, vascular and interventional procedures, using two X-ray apparatuses so that an object being examined can be observed in two planes. Each of these two apparatuses comprises an arcuated structure carrying an X-ray tube and an X-ray image receptor which arcuated structure is orbitally displaceable. One of the arcuated structures is supported on a floor base and the other is suspended form a ceiling to effectively utilize space and allow these two arcuated structure to be brought into a close proximity so that their radiation isocenters coincide with the object being imaged.

In the prior art a vertical position of the radiation axis in the ceiling suspended arcuated structure was not adjustable, therefore, a table elevation had to be adjusted to a level of object being examined and could not be adjusted to a level convenient for a medical staff.

Prior art also showed a ceiling mounted arcuated structure having an X-ray tube and an image receptor slideably mounted on extremity thereof for some limited adjustments. A disadvantage of this construction was that vhen the X-ray tube and the image receptor are moved, the isocenter of the arc no longer coincides with the radiation isocenter and for this reason the object being imaged does not remain in the center of the image, but moves away so that the patient has to be repositioned.

On the other hand, in the prior art having both X-ray units mounted on the floor and being vertically adjustable, these units could not be used individually for imaging in a single plane due to physical constrains. Also, said arrangement was more congested and provided only a limited access to a patient. And further, said arrangement did not allow for a complete imaging coverage of a patient, because the units had to be in close proximity of one another.

SUMMARY OF THE INVENTION

This invention provides an improved X-ray apparatus for imaging in one of the two planes of the bi-plane configuration, which enables vertical adjustment of the radiation isocenter, and thus, does not require the table top elevation to be readjusted or a patient to be repositioned, and further, this invention provides a uniform vertical movement.

It is therefore an object of this invention to provide an improved X-ray apparatus mounted on an overhead support for use in bi-plane imaging.

It is another object of this invention to provide an improved X-ray apparatus, which apparatus facilitates a vertical displacement of the radiation isocenter and, thus, does not require repositioning of a patient nor does it require an adjustment of the table top elevation, and therefore, allows for an adjustment of the table top elevation to the most convenient level for the medical staff for effective treatment.

And still another object of this invention is to provide an apparatus that allows to image in a single plane and that apparatus provides a full body imaqinq coverage.

A further object of this invention is to provide a smooth, uniform vertical movement of the radiation isocenter for suitable adjustments.

THE ILLUSTRATED EMBODIMENT

An X-ray imaging medical apparatus according to this invention is illustrated in the prospective drawing of FIG. 1.

This apparatus comprises : an arcuated member 1 having an X-ray tube 2 and an image receptor 3 (such as an image intensifier shovn here) mounted thereon, wherein the arcuated member 1 is mounted on a supporting member 4 in a slideable arrangement for orbital displacement. Supporting member 4 is secured to a rotatable support 5 that is mounted on a carriage assembly 6 in a rotateble arrangement about an axis generally parallel to a vertical direction.

Carriage assembly 6 comprises: a support frame 7 and a slidable support 8 coupled by a variable position coupler 9 mechanically connecting the support frame to the slidable support, which variable position coupler includes a means for maintaining a parallel relationship between the support frame 7 and the slidable support 8, such as a scissor mechanism 10, and a means for varying the distance between the support frame 7 and the slidable support 8, that may comprise a pair of timing belts or chains 11 that moves the support frame 7 relative to the slidable support 8 in a parallel shifting motion, which belts and chains engage two timing wheels or sprockets 12 coupled to one another in rotating motion and anchored to an anchoring member 13 linearly moved by an actuator 14. The slidable support 8 is slideably mounted on overhead rails for relative movement therebetween.

A ball screw actuator may be employed for moving the anchoring member.

The scissor mechanism 10 provides a rigidity and allows to move the support frame 7 into a close proximity of the slideable support 8.

The means for maintaining a parallel relationship between the support frame 7 and the slidable support 8 may be positioned in an offset arrangement to the axis of rotation of the rotatable support to provide space for mounting a support for a surgical lamp or a ceiling suspension of other medical equipment such as an X-ray table supported by an overhead structure.

The use of timing belts or chains, which timing belts and chains engage timing wheels or sprockets coupled to one another assures that the parallel shifting motion is uniform.

We claim:

1. An X-ray imaging apparatus for medical examinations comprising:
   a support member for an X-ray tube and an X-ray image receptor mounted on a carriage assembly in a rotatable arrangement about a virtual vertical axis, wherein said carriage assembly is mounted on overhead rails and includes a means for providing vertical displacement of said support member relative to said overhead rails which means comprises a scissor mechanism disposed in an offset arrangement to the axis of rotation of said support member.

2. An X-ray imaging apparatus for medical examinations comprising:

a support member for an X-ray tube and an X-ray image receptor, mounted on a carriage assembly, which carriage assembly comprises a support frame coupled to a slideable support mounted on overhead rails and a means for varying the distance between said support frame and said slideable support comprising a pair of positive motion transmission means that move said support frame relative to said slideable support in a parallel shifting motion, which positive motion transmission means engage two positive traction wheels coupled to one another in rotating motion and anchored to an anchoring member linearly moved by an actuator.

* * * * *